US009607508B2

(12) United States Patent
Lint et al.

(10) Patent No.: US 9,607,508 B2
(45) Date of Patent: Mar. 28, 2017

(54) SYSTEM INCLUDING A WIRELESS DENTAL INSTRUMENT AND UNIVERSAL WIRELESS FOOT CONTROLLER

(71) Applicant: DENTSPLY International Inc., York, PA (US)

(72) Inventors: Kevin Kenneth Lint, Seven Valleys, PA (US); Jared Witmer, Lewisberry, PA (US); Joseph Robert Reagan, Steelton, PA (US)

(*) Notice: Subject to any disclaimer, the term of this patent is extended or adjusted under 35 U.S.C. 154(b) by 0 days.

(21) Appl. No.: 14/025,949

(22) Filed: Sep. 13, 2013

(65) Prior Publication Data

US 2014/0017628 A1   Jan. 16, 2014

Related U.S. Application Data

(63) Continuation of application No. 13/084,896, filed on Apr. 12, 2011, now abandoned.
(Continued)

(51) Int. Cl.
*G08B 21/00* (2006.01)
*G08C 19/00* (2006.01)
(Continued)

(52) U.S. Cl.
CPC ............ *G08C 19/00* (2013.01); *A61C 1/0015* (2013.01); *A61C 1/0023* (2013.01); *G05G 1/46* (2013.01); *A61B 2017/00225* (2013.01)

(58) Field of Classification Search
CPC .............................. G08C 19/00; A61C 1/0023
(Continued)

(56) References Cited

U.S. PATENT DOCUMENTS 4,041,609 A   8/1977   Bresnahan et al.
4,114,275 A   9/1978   Jones et al.
(Continued)

OTHER PUBLICATIONS

International Search Report, Application No. 2011/032070, Published Apr. 12, 2011.
(Continued)

*Primary Examiner* — Jeffery Hofsass
(74) *Attorney, Agent, or Firm* — Leana Levin; Douglas Hura; David Zdurne

(57) ABSTRACT

A wireless, remote foot controller and a wireless instrument in direct communication with one another and method of operation. The remote foot controller can determine the wireless instrument in the hand of the dental professional and can determine whether the instrument is operational in an continuously variable mode or whether the instrument is operational at discrete speeds. The remote foot controller can then respond to activation by a user to provide a predetermined signal that drives the handheld unit with the appropriate signal. The remote foot controller is activated by application of pressure to the foot controller that provides tactile, sensory feedback to the user. The foot controller includes a circuit board, antenna and battery so that it is wireless. The circuit board includes communications protocol to permit the foot controller to communicate with several dental instruments. Although the foot controller is capable of controlling multiple dental instruments, it only controls one dental instrument at a time, usually the most recent device in the hands of the dental professional.

19 Claims, 9 Drawing Sheets

Related U.S. Application Data

(60) Provisional application No. 61/323,142, filed on Apr. 12, 2010, provisional application No. 61/323,129, filed on Apr. 12, 2010, provisional application No. 61/323,159, filed on Apr. 12, 2010, provisional application No. 61/323,120, filed on Apr. 12, 2010.

(51) Int. Cl.
*A61C 1/00* (2006.01)
*G05G 1/46* (2008.04)
*A61B 17/00* (2006.01)

(58) Field of Classification Search
USPC ......... 340/539.12; 606/1; 433/101; 200/86.5
See application file for complete search history.

(56) References Cited

U.S. PATENT DOCUMENTS

| | | |
|---|---|---|
| 4,417,875 A | 11/1983 | Matsui |
| 5,125,837 A | 6/1992 | Warrin et al. |
| 5,132,498 A | 7/1992 | Lee |
| 5,289,160 A * | 2/1994 | Fiorletta ..................... 340/447 |
| 5,419,703 A | 5/1995 | Warrin et al. |
| 5,534,672 A * | 7/1996 | Meagher .................... 200/61.89 |
| 5,712,460 A * | 1/1998 | Carr et al. ................... 200/86.5 |
| 5,754,016 A | 5/1998 | Jovanovic et al. |
| 6,866,507 B2 | 3/2005 | Beerstecher |
| 6,893,261 B1 | 5/2005 | Feine |
| 7,012,203 B2 * | 3/2006 | Hanson et al. ............. 200/86.5 |
| 7,439,463 B2 * | 10/2008 | Brenner et al. ............. 200/86.5 |
| 2005/0080403 A1 * | 4/2005 | Takahashi ....................... 606/1 |
| 2005/0147940 A1 * | 7/2005 | Mace ............................ 433/101 |
| 2007/0166661 A1 | 7/2007 | Brenner et al. |
| 2007/0166662 A1 * | 7/2007 | Lint et al. .................... 433/101 |
| 2009/0272221 A1 | 11/2009 | Long et al. |
| 2011/0121049 A1 * | 5/2011 | Malinouskas et al. .... 227/175.1 |

OTHER PUBLICATIONS

International Written Opinion, Application No. 2011/032070, Published Apr. 12, 2011.

* cited by examiner

1

SYSTEM INCLUDING A WIRELESS DENTAL INSTRUMENT AND UNIVERSAL WIRELESS FOOT CONTROLLER

RELATED APPLICATIONS

This application is a Continuation of pending U.S. patent application Ser. No. 13/084,896, filed Apr. 12, 2001, which is a Non-Provisional patent application of and claims the benefit of Provisional Applications Nos. 61/232,142, 61/323,129, 61/323,159 and 61/232,120, all filed Apr. 12, 2012 and now abandoned.

FIELD OF THE INVENTION

The present invention is generally directed to a system that includes a foot controller used for activating a dental or medical treatment apparatus. More particularly, the invention relates to a system that includes a wireless dental instrument and an intelligent wireless foot switch device in communication with one another, the foot controller operating in a first mode as a two-stage foot switch device or in a second mode as a continuously variable foot controller, the foot controller switching modes based upon the dental instrument with which it is in communication.

BACKGROUND OF THE INVENTION

Today, dental and medical professionals use many instruments that are controlled by control systems. For example, surgical cutting instruments, ultrasonic dental scalars, endoscopic tools, irrigation and aspiration tools, dental drills, air polishers, other low speed hygiene dental instruments, and dental prophylaxis units can be activated with foot control systems. The foot switch system typically includes a foot controller device that is placed on the floor within easy reach of the practitioner. The foot switch is used to activate a dental/medical apparatus, which includes a base operating unit, which usually is countertop-mounted and adjacent to the dental work area. The available foot pedals include both "hardwired" systems and wireless foot control systems. The base unit is activated by depressing the foot pedal, typically with a foot, which initiates communication with the base operating unit. The base operating unit is then in communication with the instrument, usually a dental instrument.

Some conventional foot switches include multi-positioned or multistaged switches. An operator depresses the pedal of the foot switch to a certain position, which causes the medical/dental apparatus to operate in a specific mode. The particular operational mode is based on the position of the switch. For example, with a two-position switch, a dental practitioner can depress the pedal to a first position so that water flows through the dental instrument for rinsing the teeth of the patient. Then, the pedal of the foot switch can be depressed to a second position so that a cleaning spray flows through the dental instrument for spraying the teeth. Such control systems provide several advantages.

First, a foot pedal device is easy to use and efficient. The dental/medical professional can activate the instrument attached to the base unit by simply depressing the foot pedal with his or her foot. Secondly, the dental/medical practitioner's hands are kept free when working with a foot pedal device. The practitioner thus can handle other instruments and accessories while treating the patient. The practitioner is better able to concentrate on performing the needed dental/medical procedure. Thirdly, as mentioned above, some conventional foot pedals are used in wireless systems, which do not run a connector cable between the foot pedal and base unit. These wireless foot pedals are used to remotely activate the base unit and attached dental/medical instruments. Many dental/medical operatory rooms contain numerous long cords, cables, wires, and the like which can become entangled easily. The entangled cords and cables take up space and may cause potential safety hazards. A wireless foot pedal system helps minimize some of these hazards.

Foot pedals can have a wide variety of structures. One two-position foot pedal of particular interest is set forth in the U.S. Pat. No. 7,439,463 to Brenner et al. issued Oct. 21, 2008, assigned to the Assignee of the present invention, and incorporated herein by reference in its entirety. The foot pedal device includes a base plate for supporting the foot pedal device on the floor, a central housing attached to the base plate, an upper cover mounted on the housing, and a connecting collar attached to the upper cover for retaining a cover on the housing while allowing the cover to move upwardly and outwardly relative to the housing. The central housing contains the first electrical switch for transmitting a first signal of the apparatus, a second electrical switch for transmitting a second signal to the apparatus, and an actuator assembly for activating the switches. The actuator assembly includes (i) an actuating plunger capable of moving in upward and downward directions, (ii) a first switch activator tab, and (iii) a second switch activator tab. An operator depresses the upper cover with his or her foot so that the cover engages the actuating plunger. As force is applied to the plunger, the plunger moves downwardly to a first position, where it engages the first switch activator tab, thereby causing the first switch to be activated. A second force applied to the plunger causes the plunger to move downwardly to a second position, where it engages a second switch activator tab, thereby causing the second switch to be activated. The foot pedal further includes a primary spring and a secondary spring. Downward pressure by the foot on the foot pedal causes the first switch to be activated. However, the primary spring resists the downward pressure thereby causing resistance that provides a tactile feel to the foot pedal. Further downward pressure causes a second switch to be activated while also causing compression of the secondary spring. This additional resistance provides further tactile feel to the operator that signals to the operator a second mode of operation has been activated. The device contemplates both wireless operation and wired operation.

Bresnahan et al., U.S. Pat. No. 4,041,609 discloses a foot pedal unit for controlling the operation of dental equipment, particularly air turbine dental instruments. The foot control unit includes a triangular-shaped base, a body portion that is supported by the base, and a removable cover. Three pivotal pedals project radially from the body portion of the foot switch in the form of a spider-like configuration. The pedals are arranged at evenly spaced positions around the circumference of the base. Each pedal includes a foot-engageable shoe connected to a pedal support member. A dentist may depress any of the pedals, and this action is transmitted to an actuator member, which also has a three arm spider-like configuration. The actuator causes a vertically movable plunger to be depressed and a control unit in the foot switch is activated. An electrical cable extending from the foot control unit to the dental instrument is used to transmit the switching signal.

Jones et al., U.S. Pat. No. 4,114,275 discloses a foot pedal for controlling the flow of compressed air to an air-driven dental instrument. The foot pedal includes a diaphragm therein for forming an air-sealed chamber, which reduces in volume upon depression of the foot pedal. As the foot pedal is depressed, air is conveyed through an air tube to an air modulating, regulator valve that is positioned away from the foot pedal device. The valve controls the flow of compressed air to the dental instrument and drives the dental instrument. Alternatively, the system can include a diaphragm-operated electrical switch that is positioned away from the foot pedal for electronically controlling the flow of air to the dental instrument.

Matsui, U.S. Pat. No. 4,417,875 discloses a foot pedal for controlling the rotational speed of an air turbine dental instrument. The foot pedal is designed such that the front part of the pedal is used for controlling high-speed rotation of the dental instrument and requires a relatively small amount of foot pressure, while the rear portion of the pedal is used for controlling low-speed rotation and requires a relatively high amount of foot pressure.

Lee, U.S. Pat. No. 5,132,498 discloses a foot pedal comprising a base covered with an upper cover and a press member. The foot pedal houses a pressure-contact switch, a pivoting rotary-type actuating member, and compression spring. The press member is pressed down in response to a foot-pressing action. This causes the actuating member to rotate downward so that a hooked portion of the actuating member is pressed against a cylindrical press button, thereby activating the foot pedal.

Warrin et al., U.S. Pat. Nos. 5,125,837 and 5,419,703 disclose an ultrasonic dental scaler unit having a dental instrument and scaling insert that can be used for scaling teeth and providing therapeutic lavage solutions to periodontal pockets in the mouth. The dental scaler unit includes a foot pedal, which is connected to the base unit by an electrical cable. The scaler unit further includes a dental instrument, which is connected to the base unit by a conduit containing electrical wires and a tube for cooling water. The base unit includes a switch that can be thrown to a first or second position. The foot pedal also can be depressed to a first or second position. The positions of the base unit switch and foot pedal make it possible for the practitioner to use the apparatus for scaling only, lavage only, or simultaneous lavage and scaling.

Jovanovic et al., U.S. Pat. No. 5,754,016 discloses an ultrasonic dental scaler system having a base unit, which is connected by a cable to a foot pedal. The scaler dental instrument, which is connected to the base unit, includes a feedback coil for controlling the amplitude and vibration of the magnetostrictive scaling insert. The amplitude and frequency of vibration of the tip of the scaling insert can be continuously adjusted to maintain constant scaling power. The foot pedal is connected to a boost enabler in the base unit by a connector cable. The foot pedal can include first and second electrical contact positions, where the second position provides a temporary boost in power to the dental instrument.

Beerstecher, U.S. Pat. No. 6,866,507 discloses a foot pedal for controlling the operation of a dental apparatus having a multifunctional dental instrument. The foot pedal includes a base plate and a relatively movable cover plate. A space between the base plate and cover plate forms a fluid tight hollow cavity. Multiple press switches are arranged in the hollow cavity. The press switches are made from a printed circuitry, which is sandwiched between first and second carrier foils. A signaling line connects the foot pedal to the electronic control systems of the dental apparatus.

Feine, U.S. Pat. No. 6,893,261 discloses a foot pedal for controlling an ultrasonic dental scaler. The foot pedal incorporates the circuitry for controlling the vibrational frequency of the scaling insert and can also provide water and light to a remote head unit. A cable bundle connects the foot pedal to the remote head. The foot pedal housing is connected to a power supply and is additionally connected to a water source. The foot pedal housing can also include a light source such as an argon lamp. The remote head can be attached to a dental treatment chair or it may be carried on the belt of a dentist or dental hygienists.

What would be useful is a wireless, remote foot controller that recognizes the dental instrument in the hands of the dental professional and determines whether it should generate a signal that is responsive to pressure to provide a signal that varies in proportion to the directional movement of the foot controller by the foot, thereby driving a dental instrument in an infinitely variable manner or whether it should be responsive to the directional movement of the foot controller to provide a plurality of discrete signals that are activated by the directional movement of a foot controller by the foot, thereby driving the dental instrument at discrete speeds. Ideally, the foot controller should provide a tactile feel to the user so that the user can obtain a sensory feel of the speed that the hand unit is being driven based on the pressure applied by the user's foot. The foot controller should be in communication with the dental instrument so that the foot controller can determine whether the dental instrument is controlled based on being driven by discrete signals or in an infinitely variable fashion.

SUMMARY OF THE INVENTION

The present invention provides a system that includes a wireless, remote foot controller and a wireless instrument in direct communication with one another. The remote foot controller can determine whether the wireless instrument is in the hand of the dental professional and can determine whether the instrument is operational in a continuously variable mode or whether the instrument is operational at discrete speeds. The remote foot controller can then respond to activation by a user to provide a predetermined signal that drives the handheld unit with the appropriate signal. The remote foot controller is activated by application of pressure to the foot controller that provides tactile, sensory feedback to the user. The foot controller includes a circuit board, antenna and battery so that it is wireless. The circuit board includes communications protocol to permit the foot controller to communicate with other RF-operated dental instruments. The foot controller includes memory that may be separate or mounted or included as an integral part of the circuit board. The circuit board has associated with it a microchip/controller, which may be integral with the circuit board, mounted on the board or otherwise associated with the circuit board. The microchip may include the previously noted memory for the unit. Software or firmware controls the operation of the foot controller. The circuit board and battery are enclosed within a foot controller housing. The foot controller is capable of controlling multiple devices, although it only controls one device at a time, the most recent device in the hands of the dental professional.

The dental instrument includes a circuit board, an antenna and a battery so that it is wireless, at least with regard to its communicative capability. The dental instrument at least transmits signals to the foot controller. The dental instrument further may be adapted to receive tools such as cutting tools or other specialty tools to permit the dental instrument to be utilized as a special purpose device adapted for a particular function. Tools are readily attached and detached from the dental instrument. The dental instrument further includes a motion detecting device so that the dental instrument will transmit a signal to the foot controller indicating that it is operational. The dental instrument may be a completely wireless device or may include connections to a source for air, water or both.

The foot controller is activated by an operator depressing it with foot pressure. It may operate in a switch mode, in which the foot controller provides a signal resulting from the activation of one or more switches as a result of depressing the foot controller. The foot controller may also operate in a continuously variable mode, in which the foot controller provides a signal proportional to the distance the foot controller is depressed.

The foot controller is capable of communication with multiple devices and determines which of the multiple devices it will control and in which mode it will operate as a result of communications with the most recent dental instrument in the hand of the dental professional. The foot controller will receive a signal from the dental instrument in the hand of the dental professional. The foot controller will recognize whether the signal is from a dental instrument that it is one configured to operate with the controller and, if so, the mode that the foot controller must operate in so that the proper signal is provided to the dental instrument.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

Figure 1:
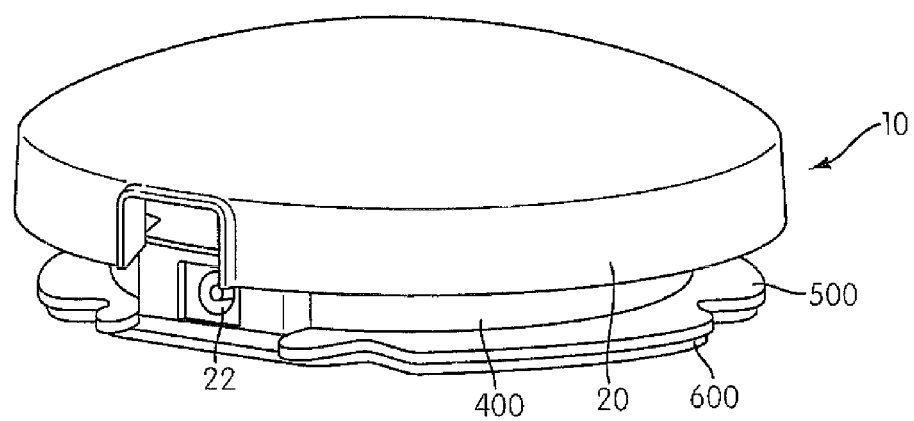
FIG. 1 is a perspective view of the foot controller of the present invention.

Figure I is a perspective view of a cordless foot controller 10 of the present invention. A cover 20 hides the foot controller internals from view, although a charge connector 22 is visible. Charge connector 22 accepts an electrical cord for recharging a battery positioned inside cover 20. Foot controller 10 sits on a bottom plate 500 which is spaced from cover 20. Attached to bottom plate 500 is an anti-skid rubber bottom 600, which provides sliding resistance for foot controller 10 and prevents skidding as it is used on a floor. Bottom plate 500 supports upper housing 400.

Figure 2:
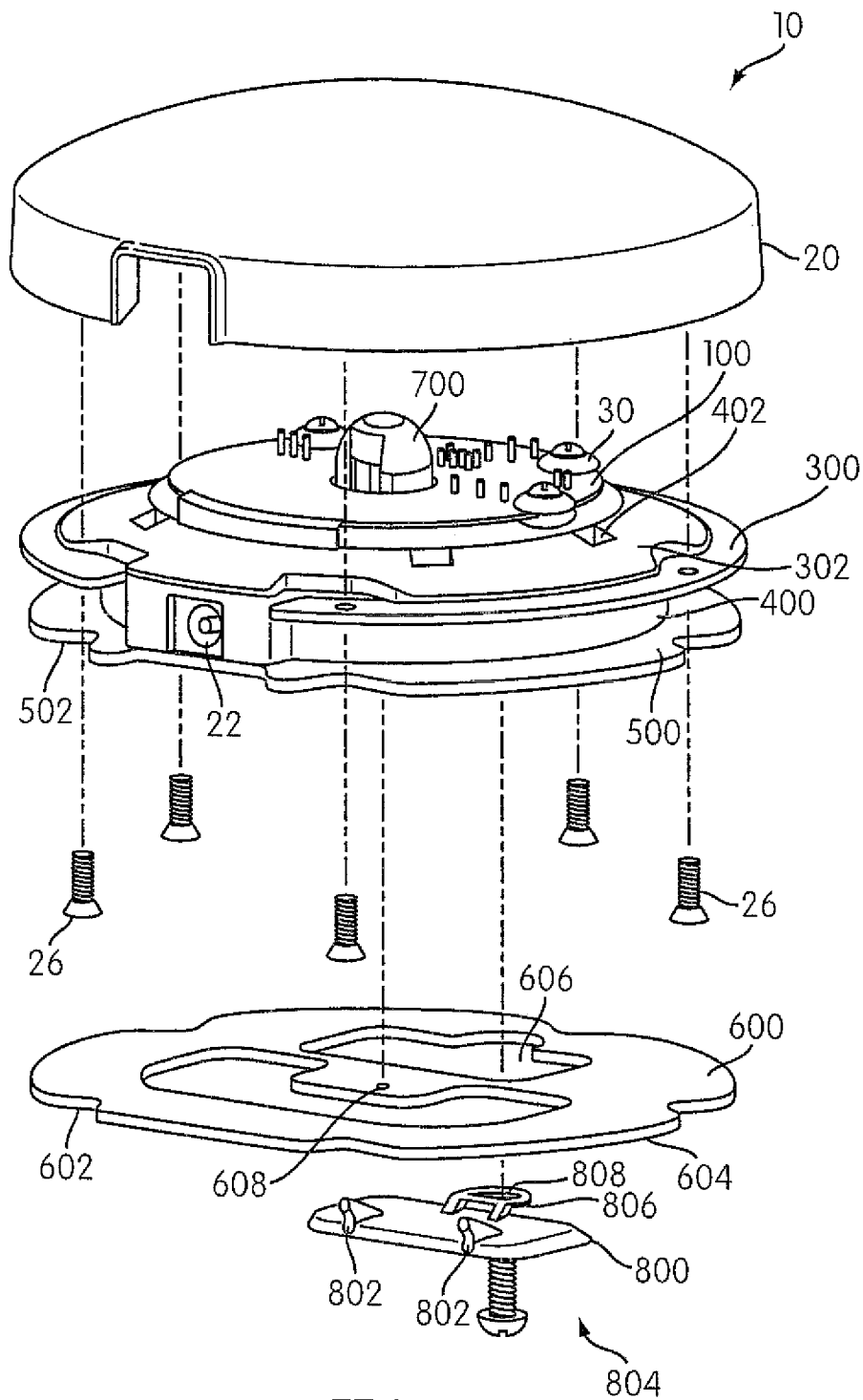
FIG. 2 is a partially exploded view of the foot controller of FIG. 1.

FIG. 2 is a partially exploded view of cordless foot controller 10, displaying the internal arrangement within cover 20. Printed circuit board (PCB) assembly 100 overlies upper housing 400, which is spaced from bottom plate 500 by holding ring 300. Screws 26 are utilized to fasten holding ring 300 to cover 20, sandwiching upper housing 400 therebetween. PCB assembly 100 is attached to upper housing 400 by fastener assemblies 30. Charge connector 22 is visible on a wall of upper housing 400. Plunger housing assembly 700 extends through an aperture in PCB assembly 100. Screws 26 extend through apertures 302 in holding ring 300 and are captured in corresponding female threaded regions (not visible) that may be molded into cover 20. Scallops 502 in bottom plate 500 are provided for assembly purposes, so that a tool such as a screwdriver can be inserted to provide full engagement with screws 26. Cut-outs 402 in upper housing 200 are provided for additional clearance for passage of screws through upper surface 404, and depending upon design of upper surface 404 and upper housing 400 may not be necessary. Although anti-skid rubber bottom 600 is attached to bottom plate to complete assembly, anti-skid rubber bottom 600 may include scallops 602 that permit subsequent access to screws 26 without removal of anti-skid bottom plate 600, since anti-skid rubber bottom 600 may be permanently assembled to bottom plate 500.

Access cover 800 is also visible in FIG. 2. Access cover 800 slides through access aperture 606 in anti-skid rubber bottom 600 and into an access aperture (not visible in FIG. 2) in bottom plate 500. Access cover 800 includes at least one tab 802 that extend into one side of aperture 506 in bottom plate 500, while screw 804 slides through aperture 808 in lock tab 806 and into a female threaded receiver (not visible) in upper housing 400, thereby locking access cover 800 in place. Access cover 800 provides access to the interior of foot controller 10 through aperture 606 and the aperture in bottom plate 500, and importantly, to a bottom surface of PCB assembly 100 by simply removing screw 804 and sliding access cover 800 from bottom plate 500, without the need to completely disassemble bottom plate 500 from cover 20, unscrewing screws 26 from cover 20 and fastener assemblies from upper housing 400. Access is available to the interior of cordless foot controller. Such access means that it is not necessary to remove PCB assembly 100 from upper housing 400 in order to expose the bottom surface of PCB assembly 100. Switches (such as DIP switches) or a connector to permit reprogramming of the unit can be provided along the bottom surface of PCB assembly 100. Furthermore, battery 38 can be replaced through access cover 800. A second screw (not shown) also may be provided for anti-rotation and fastening. Cordless foot controller 10 is free to move along a floor without skidding, and cover 20, as will become clear, can move with respect to the remaining portions of the foot controller 10.

Figure 3:
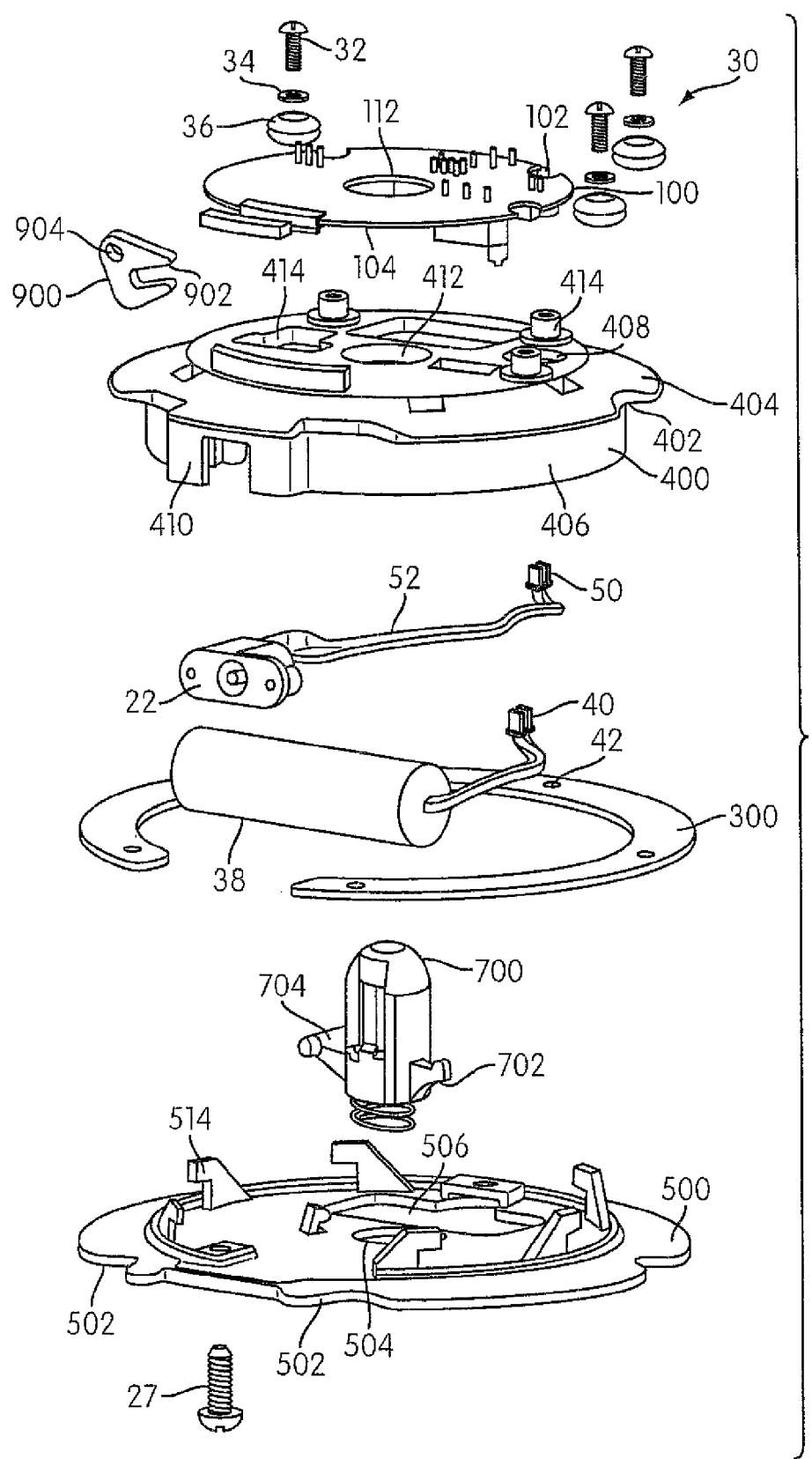
FIG. 3 is a fully exploded view of the printed circuit board assembly, the upper housing and lower housing of the controller of the present invention.

FIG. 3 is a further exploded view of upper housing 400, bottom plate 500 and portions of foot controller 10, either attached to upper housing 400 and bottom plate 500 or captured within upper housing 400 and bottom plate 500.

Upper housing 400 is shown having an upper surface 404 and a vertical surface 406. A charge connector aperture 410 penetrates vertical surface 406 that receives charge connector 22. Upper surface 404 includes a central aperture 412, through which plunger assembly 700 extends. Upper surface 404 also includes a plurality of female thread housings 408. Upper surface further includes additional apertures 414, whose purpose will be readily apparent below.

Also shown in FIG. 3 is PCB assembly 100. PCB assembly 100 includes a plurality of scallops 102 and has a mounting surface 106 and an opposite surface 104 from mounting surface 106. Opposite surface 104 and mounting surface 106 are shown in detail in FIGS. 4 and 5 and further discussed below. PCB assembly 100 is assembled to upper housing 400 using a plurality of fastener assemblies 30. Each fastener assembly 30 comprises a screw 32, a washer 34 and grommet 36. Each grommet 36 is assembled along the edge of PCB assembly 100 at each scallop 32. Grommets 36 are then assembled over female thread housings 408. Washers 34 are assembled over grommets 36 and screws 32 secure fastener assemblies 30 to 408, thereby securing PCB assembly 100 to upper housing 400, while maintaining vibration isolation.

Figure 9:
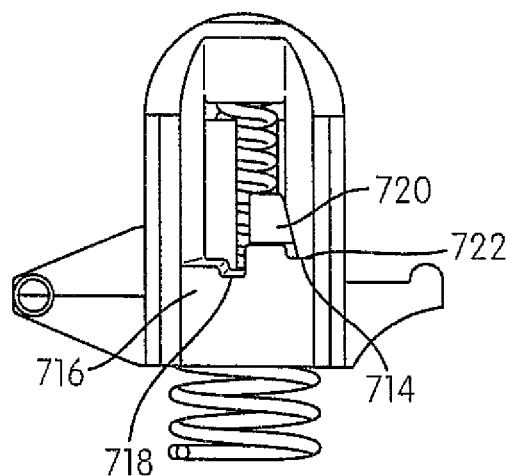
FIG. 9 depicts the plunger housing assembly with the spring retainer in a first position.
Figure 10:
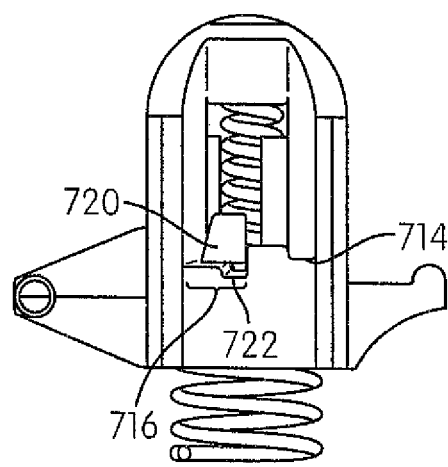
FIG. 10 depicts the plunger housing assembly with the spring retainer in a second position.

FIG. 3 also shows bottom plate 500, plunger housing assembly 700, battery 38, charge connector 22 and holding ring 300. Plunger housing assembly 700 sits on bottom plate 500, extending through holding ring 300, upper housing central aperture 412 and PCB assembly center aperture 112. Plunger housing assembly 700 includes a plunger housing 701 having a plunger arm 702 extending away from housing 701 in a first direction and a potentiometer coupling arm 704 extending away from housing 701 in a second direction. Plunger housing 701 has a hollow interior that accepts a primary spring 708 having a first spring constant. Nested inside primary spring 708 is a secondary spring 710 having a second spring constant. A spring retainer 712 separates primary spring 708 from secondary spring 710. An access aperture 504 in bottom plate 500 provides access to plunger housing assembly 700 to engage spring retainer 712, FIG. 6. Spring retainer 712 is moveable from a first position depicted in FIG. 9 to a second position depicted in FIG. 10. Plunger housing 701 includes a first slot 714 and a second slot 716 having a downwardly extending gap 718 at the right end of second slot 716 in FIGS. 9 and 10. Spring retainer 712 includes a tongue 720 having a downwardly extending projection 722. As shown in FIG. 9, first slot is sufficiently wide to accept only downward projection 722 of tongue 720, thereby locking spring retainer 712 in the first position. In FIG. 10, second slot 716 is sized to accept tongue 720, and gap 718 is sized to accept downward projection 722, locking spring retainer 712 in the second position as shown.

Figure 11:
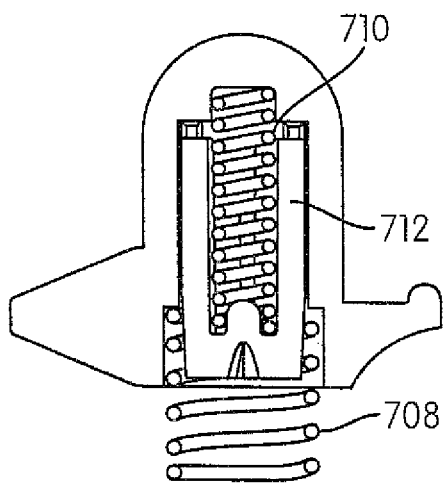
FIG. 11 depicts the plunger housing assembly with the spring retainer in a first position, with the secondary spring fully compressed.
Figure 12:
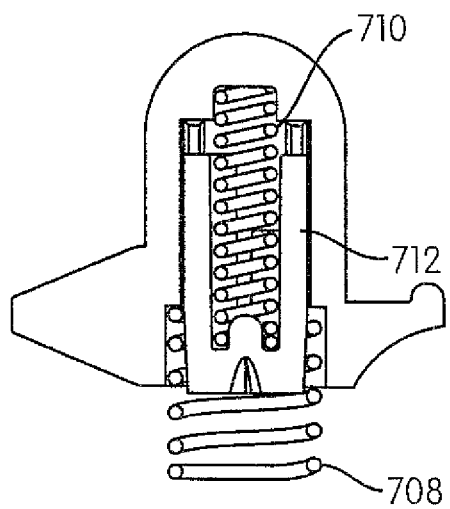
FIG. 12 depicts the plunger housing assembly with the spring retainer in a second position, with the secondary spring uncompressed.
Figure 13:
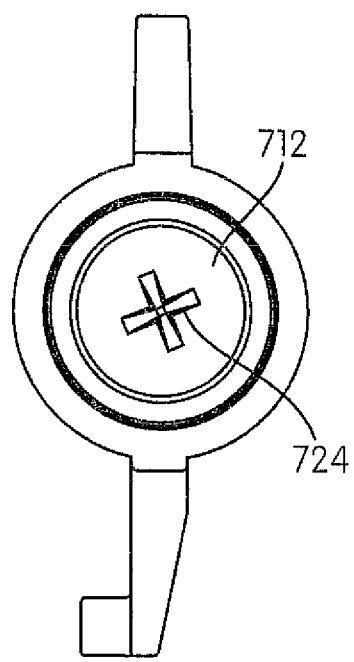
FIG. 13 depicts the plunger housing assembly showing slots in bottom of the spring retainer enabling movement of the spring retainer from a first position to a second position.

When spring retainer 712 is locked in place in the first position as shown in FIG. 11, secondary spring 710 is compressed and resistance to downward movement (provided by the foot of an operator) is only provided by primary spring 708. When spring retainer is locked in place in the second position, as shown in FIG. 12, secondary spring is in an uncompressed state. Resistance to downward movement is first provided by secondary spring 710, until it is fully compressed. When secondary spring 710 is fully compressed, further resistance to downward movement is provided by primary spring 708. Since secondary spring 710 and primary spring 708 have different spring constants, the operator will observe the difference in resistance as resistance to downward movement is shifted from secondary spring 710 to primary spring 708. As shown in FIG. 13, spring retainer 712 is readily moved from being locked in place in first position to being locked in place in second position by slots 724 in bottom of spring retainer 712. A screwdriver or cross-shaped tool is inserted into one or both slots and, a force is applied to depress retainer 712 inward. Spring retainer 712 can then be rotated from one position to the other and the force is released, locking spring retainer into position.

Plunger housing assembly 700 includes two arms. First arm is a plunger arm 702 while second arm is a potentiometer coupling arm 704. Potentiometer coupling arm 704 includes a shaft 706 that extends at an angle, about 90°, away from arm 704. Also depicted in FIG. 3 is a potentiometer adaptor lever 900. Lever 900 includes a slot 902 and an aperture 904. When assembled, potentiometer coupling arm 704, plunger arm 702 and lever 900 are positioned below printed circuit board assembly 100, even though a portion of plunger housing assembly 700 may protrude through central apertures 112, 412. Slot 902 of potentiometer adaptor lever 900 fits over potentiometer coupling arm 704 of plunger housing assembly 700. Any movement of plunger housing assembly 700 will cause movement of potentiometer coupling arm 704 which will cause movement of potentiometer adaptor lever 900 resulting in rotational movement of aperture 904 as slot 902 moves. Potentiometer shaft 132 is assembled through aperture 904 of potentiometer adaptor lever 900. Rotational movement of aperture 904 causes rotation of potentiometer shaft 132, which also controls the RF signal sent by the RF unit (A-D converter converts the analog signal generated by this rotation into a digital signal which is transmitted by a transceiver antenna system). Motion of plunger arm 702 is used to activate and inactivate first switch 160 for the binary mode. First switch for binary mode may also function as a wake-up switch for the unit, or the wake-up switch may be provided as a separate switch. An optional second switch 180 for the binary mode also may be provided. First switch 160, and switches 170 and 180 when provided, are located on PCB assembly 100, FIGS. 7 and 8.

Also depicted in FIG. 3 is battery 38 and charge connector 22. A first electrical connector 40 is attached to battery 38 via first wire 42. A second electrical connector 50 is also attached to charge connector 22 via a second wire 52. (When assembled, fastener assemblies 30 attach PCB assembly 100 to female thread housings 408 in upper housing 400, discussed above.). Screws 26, FIG. 2, secure holding ring 300 to cover 20, capturing upper housing 400 and holding ring 300. Bottom plate 500 is assembled to upper housing 400 by inserting notched flanges 514 through additional apertures (not visible) and rotating. On rotation, notched flanges 514 positively engage cross-members (not visible) in upper housing 400 to lock bottom plate 500 in position with respect to upper housing 400. Fastener 26 attaches bottom plate 500 to upper housing 400, preventing further rotation of one with relation to the other, while capturing holding ring 300 therebetween. Scallops 502, 402 provide access as required during assembly. Charge connector 22 is seated in charge connector aperture 410 by any convenient means. It may be held in, for example, with fasteners, or it may be held in place by a snap-fit. Battery 38 and wires 42 and 52 reside in the space between upper housing 400 and bottom plate 500.

Figure 4:
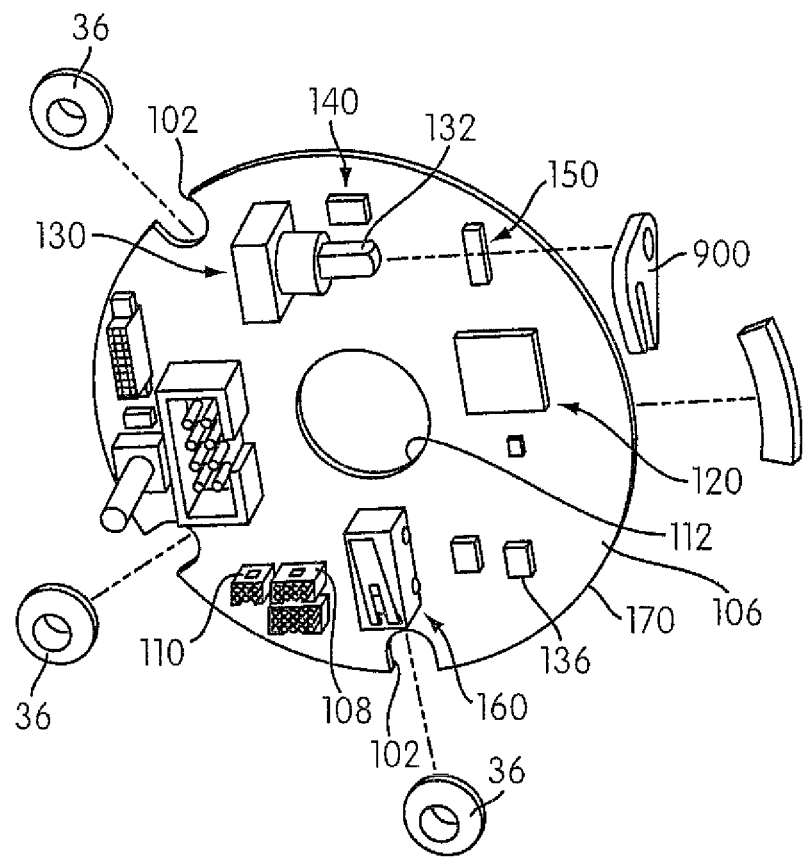
FIG. 4 is a top view of the upper surface of the printed circuit board assembly.
Figure 5:
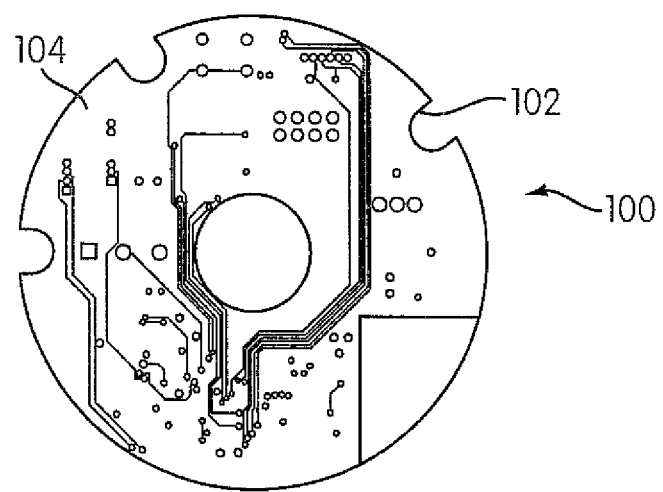
FIG. 5 is a partially exploded view of the lower surface of the printed circuit board assembly.

FIGS. 4 and 5 disclose the mounting surface 104 and the opposite surface 106 of printed circuit board assembly 100. FIG. 5 depicts the traces that are characteristic of the surface opposite a mounting surface of a printed circuit board assembly. The printed circuits on the printed circuit board assembly in cordless foot controller 10 are the subject of co-pending patent application Ser. No. 14/042,813, filed Oct. 1, 2013, and incorporated herein by reference.

FIG. 4 is a partially exploded view of mounting surface 106 of PCB assembly 100. All components assembled to mounting surface 106 of PCB assembly 100 are connected to the traces on opposite surface 104 of PCB assembly 100 in a conventional manner.

Mounting surface 106 includes a first connector 108 that mates with first electrical connector 40 attached to battery 38 that provides power to PCB assembly 100. A second connector 110 mates with second electrical connector 50 attached to charge connector 22 that enables battery 38 to be recharged when charge connector 22 is connected to a 5 Volt DC power source with a converter that connects to a standard 120V outlet. Microprocessor 120 controls the operation of cordless foot controller 10. Microprocessor 120 may include memory, various input and output ports and may include firmware. Microprocessor 120 includes an integrated transceiver, although if desired, a separate transceiver may be provided on PCB assembly 100 or separately located within foot controller 10. Microprocessor 120 is programmed to control the operation of foot controller 10 and to communicate with one or more dental instruments via antenna 150. Potentiometer 130 also is attached to mounting surface 106. Potentiometer 130 includes a shaft 132 extending at a right angle away from the potentiometer body. Shaft 132 includes a flat that mates with a flat in aperture 904 of potentiometer adaptor lever 900 so that any motion of potentiometer adaptor lever 900 results in rotational movement of shaft 132 of potentiometer. As noted above, potentiometer adaptor lever 900 will move when plunger housing assembly 700 moves, as potentiometer coupling arm 704 is coupled to potentiometer adaptor slot 902. Potentiometer 130 is a very precise instrument, and shaft position controls a resistance reading which is indicative of the position of the foot controller. When foot controller 10 is in potentiometer mode, the resistance reading from potentiometer 130 is provided to microprocessor 120 which determines the precise positioning of the foot controller 100 and communicates this information via antenna 150 to an active dental instrument.

An accelerometer 140 is provided that detects orientation of the cordless foot controller 10 and notifies microprocessor 140 when foot controller is in a substantially horizontal position. When foot controller is not in a substantially horizontal position, the foot pedal will not operate. The notification from the accelerometer may either be a signal or a lack of signal when the controller is in the proper position. When notification is provided to the microprocessor 120 within a predetermined time, microprocessor 120 is programmed to put foot controller 10 into a sleep mode. As shown in FIG. 4, a wake-up switch 160 is provided. The wake-up switch 160 provides a signal when foot controller 10 is moved. The signal from wake-up switch 160 to microprocessor 120 will cause the microprocessor to "wake-up" or restore power from battery 38 to the circuits on PCB assembly 100. A signal from a dental instrument to foot controller 10 received by transceiver, which in the embodiment shown, also wakes up foot controller 10. Once foot controller is active, accelerometer 140 can determine the orientation of foot controller 10 and whether operation can continue. For example, when foot controller 10 is being moved from a first location to a second location, accelerometer 140 can determine whether foot controller 10 has been moved into a substantially non-level position, and will notify microprocessor 120 to place foot controller 10 into a sleep mode. Power will not be restored until accelerometer 140 notifies microprocessor 120 that foot controller 10 is in a substantially horizontal orientation. Additional apertures 414 in upper housing 400 are provided to accept and house connectors 108, 110 microprocessors 120, accelerometers 140 and other apparatus attached to PCB mounting surface 106.

Figure 6:
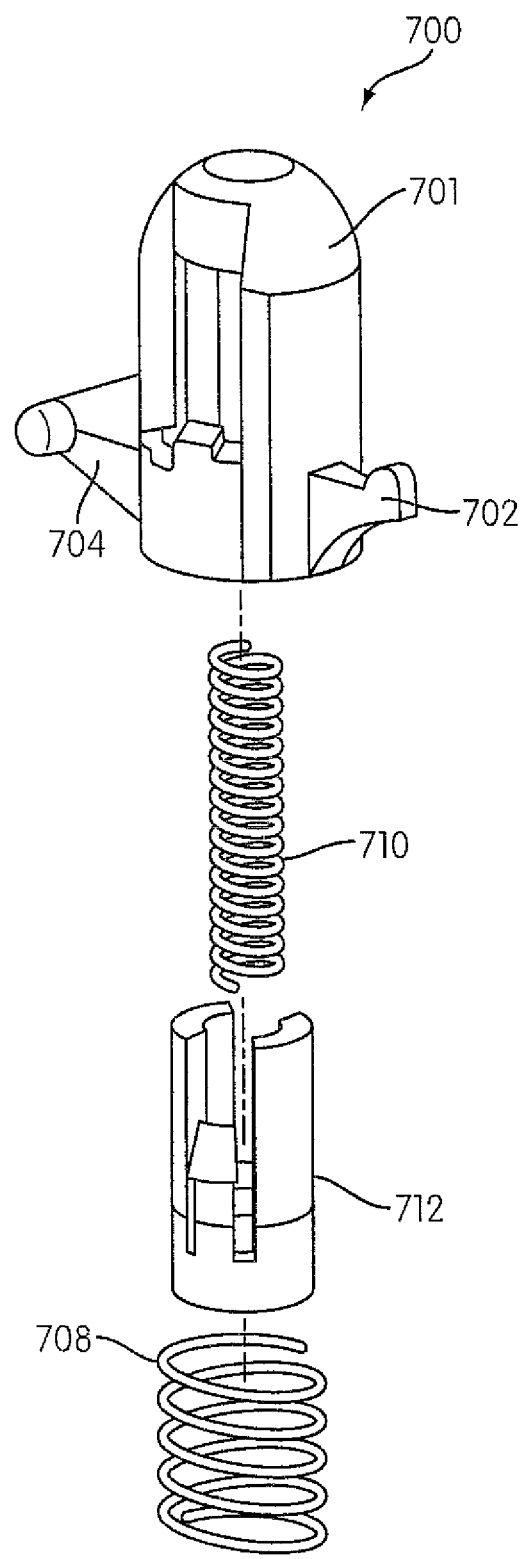
FIG. 6 is an exploded view of the plunger housing assembly.

FIG. 6 is an exploded view of plunger housing assembly 700. Plunger housing assembly 700 functions as a pressure feedback mechanism to an operator when foot controller 10 is operated either as an infinitely variable switch or as a discrete multi-position switch. Springs 708, 710 provide two distinct resistances to downward pressure to the end user due to the two distinct spring constants of springs 708, 710, although one of the springs, 710 can be inactivated, as previously discussed, so that only a single resistance is perceived. When footswitch is operating as a continuously variable switch, referred to hereinafter as "potentiometer mode operation", plunger housing assembly 700 permits the footswitch to send signals to a dental instrument to control the speed of the dental instrument in a continuously variable fashion. When operating as a multi-position switch, described herein as a two-position switch, although more than two positions may be incorporated into plunger housing assembly 700, if desired, plunger housing assembly 700 permits the foot controller 10 to send signals to a dental instrument. The dental instrument and its logic will then receive the signals and control the speed or power of the dental instrument at one of two predetermined speeds or power levels.

Figure 7:
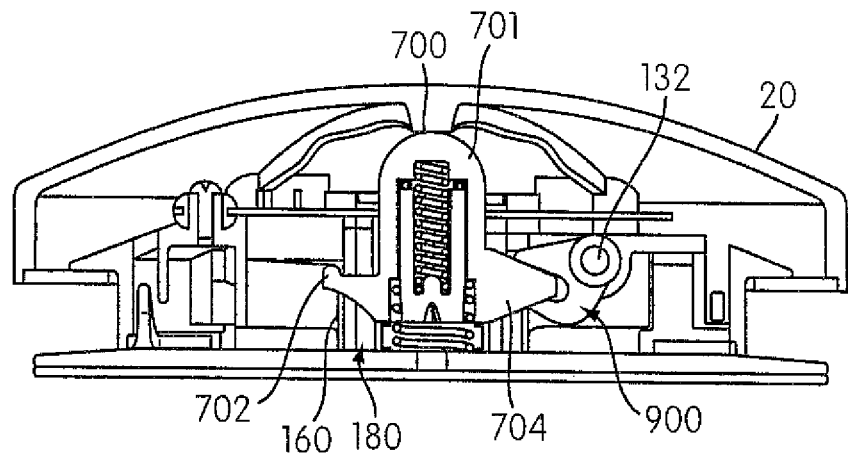
FIG. 7 is a cross-sectional view of an assembled cordless foot controller in an inactivated position.
Figure 8:
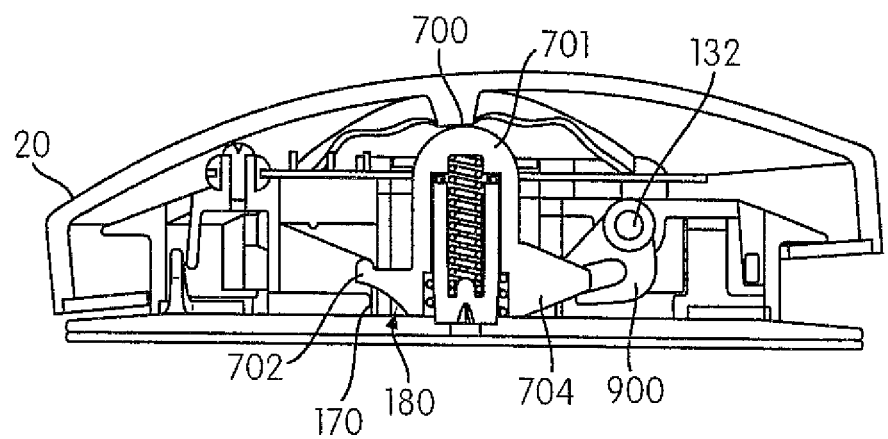
FIG. 8 is a cross-sectional view of an assembled cordless foot controller in a fully activated position.

FIGS. 7 and 8 depicts cordless foot controller 10 in cross-section, FIG. 7 depicting cordless foot controller 10 inactivated and FIG. 8 depicting cordless foot controller 10 activated.

Cordless foot controller 10 will operate with a plurality of dental instruments. A learn mode is activated on cordless foot controller. This can be accomplished by any available technique. Simple techniques involve toggling a switch between an operational mode and a learn mode, pressing a momentary button on the foot pedal or any other convenient means. A dental instrument also is placed in a learn mode. This learn mode also can be by any convenient means, such as by means of a switch button, a repeated action or a sensing of a specific position through the use of an accelerometer. When placed in the learn mode, a dental instrument transmits a signal to foot controller 10 that provides an identification code to foot controller 10 as well as communication mode. The communication mode identifies whether the dental instrument operates in an infinitely variable switch mode or in the multi-speed switch mode, as well as any additional communication information that will be sent and received with each signal transmission. For simplicity of discussion, the two-spring plunger housing assembly 700 only provides a binary switch mode, but foot controller 10 can be expanded to provide more than two speeds. The dental instrument identification code and its communications information is received by the transceiver included with foot controller 10 and is stored in the memory of foot controller 10. As soon as this information is stored in memory, the identification code of foot controller 10 is transmitted to the dental instrument, where the foot controller identification code is stored in the memory of the dental instrument. As soon as the foot controller identification code is stored in the memory of the dental instrument, the dental instrument may emit an audible or visual signal to indicate that programming is complete so that the dental instrument and foot controller can be switched back to an operational mode. The learn mode is now complete. While the foot controller can store in memory identification and operational codes for multiple dental instruments, each dental instrument can only store a single foot controller identification code in memory. The number of dental instruments that a single foot controller 10 can store in memory is dictated by the memory capabilities of foot controller 10 and the software. While cordless foot controller 10 can be programmed to control a plurality of dental instruments, each dental instrument can only be programmed to be operational with a single foot controller 10 at any one time.

A cordless dental instrument will be in sleep mode to conserve battery power. However, once a dental instrument is picked up, a wake up switch or accelerometer will cause the dental instrument to be activated. The dental instrument will transmit its identification code. The dental instrument identification code will be received by foot controller 10. The dental instrument identification code will be compared to the stored identification codes in memory, which is typically associated with memory 120 on PCB assembly 100 of foot controller 10. If the dental instrument identification code is recognized, foot controller 10 will be placed into the appropriate operational mode, either continuously variable switch mode or multi-speed switch mode depending upon the operational code associated with the dental instrument. Microprocessor 120 will place foot controller 10 into a mode to communicate with this dental instrument and it will remain in this mode until another dental instrument is activated. If a second dental instrument is activated, it will transmit its identification code in the same fashion. In this manner, when more than one dental instrument is active, the foot controller queries the activity level of all active devices, and communicates with the device that has experienced the most recent activity. If the identification code of the second dental instrument is recognized, foot controller 10 will replace the first dental instrument in its microprocessor 120 and will operate the second dental instrument. Microprocessor 120 of foot controller 10 is programmed so that it will always utilize the identification code of the most recently active dental instrument. In this manner, when more than one dental instrument is active, the foot controller queries the activity level of all active devices, and communicates with the dental instrument that has experienced the most recent activity.

Foot controller 10 also will go into a sleep mode as a result of inactivity in order to conserve battery power. Foot controller 10 can be brought out of sleep mode by different mechanisms. When foot controller is brought out of sleep mode as a result of a signal from its accelerometer, foot controller 10 sends a signal out to all of the dental instrument instruments with which it has been synchronized to determine which dental instruments are awake and which dental instrument has the highest level of activity as determined by dental instrument accelerometers. Foot controller 10 then places the dental instrument having the highest activity level in its operating queue and communicates with that dental instrument until foot controller 10 is fully released.

Foot controller 10 retains synchronization information related to operation of particular dental instruments in memory. If the last dental instrument handled is one that operates in multi-switch mode, such as an ultrasonic scaler available from Dentsply International, a CAVITRON® that operates in a binary switch mode, foot controller 10 will have recognized it from its identification code that it operates in binary switch mode. Microprocessor 120 places foot controller 10 into binary switch mode. As foot controller 10 is depressed by an operator, it physically moves from the inactivated position in FIG. 7 to the activated position in FIG. 8. Operation of foot controller 10 in this mode is fully described in U.S. Pat. No. 7,439,463 issued Oct. 21, 2008, assigned to the assignee of the present invention, and incorporated herein by reference. The depression of cover 20 by application of foot pressure of a dental professional causes downward movement of plunger housing 701 as well as plunger arm 702. Partial downward movement of plunger housing 701 and plunger arm 702 activates switch 160 on printed circuit board 100. Switch 160 may have more than one switch position that can be activated. It will be understood by those skilled in the art that a multi-position switch may be interchangeably replaced by a plurality of discrete single switches, if desired. The downward movement is resisted by primary spring 708, which provides tactile feedback to the dental professional. The activation of switch 160 results in microprocessor 120 generating a first signal that is transmitted by antenna 150 and received by ultrasonic scaler, causing scaler to operate at a first, preselected power level. While this discussion is directed to a sealer, a different type of the dental instrument, such as drill, may operate at a first, preselected speed.

Continued and increased application of foot pressure by the dental professional causes plunger arm 702 to move switch 160 past a preset limit, activating the second switch position, resulting in transmission of a second mode of signals, activating a second switch 180 or moving the potentiometer 130 past a threshold position. This mode is activated when secondary spring 710 is fully depressed. Further downward movement of plunger housing is now resisted by both primary spring 708 and secondary spring 710. FIG. 8 depicts foot controller 10 in this position. The increased resistance resulting from resistance by both springs provides tactile feedback to the user to indicate activation of the second mode. Downward movement is initially resisted by primary spring 708, which provides tactile feedback to the dental professional. Activation of second switch 180, or a threshold position on the potentiometer, provides a signal to the microprocessor 120 resulting in microprocessor 120 generating a second signal or set of signals that is transmitted by antenna 150 and received by ultrasonic scaler, causing scaler to operate at a second, preselected power level, or if different type of dental instrument, to operate at a second speed.

Release of pressure from foot controller 10 will result in cessation of signals from foot controller 10. If foot controller 10 is not activated for a predetermined time, it will go to sleep to conserve battery power. The predetermined time before foot controller goes into a sleep mode may be pre-programmed into the memory on the PCB assembly 100, or manual selection capabilities of preselected times may be provided on the unit.

If a different dental instrument is picked up by the dental professional, for example a low speed drill that operates in the infinitely variable speed mode, for example, the dental instrument will be awakened by handling and will broadcast its identification code and await a signal from the foot controller, requesting status as previously discussed. The antenna and receiver of foot controller 10 will receive the signal and send it to the microprocessor, which will compare it to the identification codes stored in its memory. If microprocessor 120 recognizes the identification code, it will immediately replace the identification code of the ultrasonic scaler, which had been in its current operation register, with that of the low speed drill. The memory will also indicate that low speed drill operates in the infinitely variable speed mode, and the microprocessor will activate the potentiometer of the foot controller so that the controller will operate in the infinitely variable mode.

Foot controller 10 is now in the potentiometer mode and is activated by an operator by depression of cover 20 from the inactivated position in FIG. 7 to the activated position in FIG. 8. The depression of cover 20 by application of foot pressure of a dental professional causes downward movement of plunger housing 701 which causes potentiometer coupling arm 704 to move downward. Slot 902 of potentiometer adaptor lever 900 is fitted to potentiometer coupling arm 704. Downward movement of potentiometer coupling arm 704 causes potentiometer adaptor lever 900 to rotate. Because potentiometer shaft 132 is received in aperture 904 of potentiometer adaptor lever 900, rotation of potentiometer adaptor lever 900 causes rotation of potentiometer shaft. This causes a signal to be generated by the potentiometer that is dependent upon the position of potentiometer shaft 132. Microprocessor 120 processes the signal generated by potentiometer 130 causing microprocessor to broadcast a signal via antenna 150 that is received by dental instrument. The signal is received and processed by a microprocessor in the dental instrument and the speed of the motor in the dental instrument is adjusted as a function of the processed signal.

Continued and increased application of foot pressure by the dental professional moves cover 20 in a downward direction causes downward movement of plunger housing 701, causing potentiometer coupling arm 704 to move downward, which in turn results in potentiometer adaptor lever 900 to rotate and potentiometer setting to change as potentiometer shaft 132 rotates with potentiometer adaptor lever. FIG. 8 depicts foot controller 10 fully in this mode. This changes the signal sent to the microprocessor 120, which in turn changes the signal generated by microprocessor 120 that controls the speed of the dental instrument. Of course, primary spring 708 and secondary spring 710 continue to provide tactile feedback to the user. These springs are helpful in assisting the user in determining when the maximum speed capabilities of the handheld unit are being approached and when lower speed capabilities are being accessed. As the user becomes more familiar with foot controller 10, the user also will develop a sense of the operational speed of a particular dental instrument with the distance that cover 20 is depressed. When pressure is released from foot controller 10, returning foot controller 10 to the position depicted in FIG. 7, a signal is sent to microprocessor 120 that pressure has been released, and a signal is broadcast by the antenna and received by the dental instrument indicating cessation of power to the dental instrument motor. Also, microprocessor 120 is placed in a mode awaiting additional input, either with respect to foot controller motion or from one of the dental instruments that are programmed into its memory. If no additional input is received within the preselected time, the foot controller 10 will go into a sleep mode until awakened.

Although the infinitely variable speed mode operation is described using a potentiometer, one skilled in the art will also recognized that the infinitely variable speed mode can be approached by a series of closely aligned switches that are activated either mechanically, magnetically or electrically. As foot controller 10 is depressed or released, the switches are activated or inactivated, each switch sending different signals to microprocessor which are processed. The signals are directly correlated with the distance that cover is depressed and correlates to a speed. Microprocessor 120 sends a signal that is broadcast by the antenna system and is received by the dental instrument to operate at the designated speed. This mode of operation differs from the binary switch mode because, although each switch generates a signal indicative of a predetermined, discrete speed, the signals are integrated, as is the speed so that preferably, the change in discrete speeds is slight so as to provide a sense of a smooth, continuous transition to the operator.

Although a binary switch mode has been discussed with reference to a switch having more than one position, or by use of a plurality of switches, a binary switch mode can also be accomplished solely with the potentiometer and appropriate software. The potentiometer setting can be determined and compared to a read value or to a trip or threshold value. If this value is exceeded, the microprocessor sends the appropriate switch code. When using a potentiometer, a microprocessor, properly programmed, can determine potentiometer position and resolve it into discrete numbers through use of an analog to digital converter available on the circuit board 100 or included in the microprocessor.

When a plurality of switches is used to provide an infinitely variable speed mode, the switches can be integrated into the binary speed mode so that microprocessor 120 processes signals received by a first series of switches to result in a first signal to be transmitted to the dental instrument and signals received by a second series of switches to result in a second signal to be transmitted to the dental instrument. Alternatively, a dental instrument that operates in a binary speed mode can include a microprocessor that receives a signal in a first set of signals and operates the dental instrument at a first speed, but operates the dental instrument at a second speed when a signal within a second set of signals is received.

Although the operation of foot controller 10 is described above for use with cordless dental instruments, the use of foot controller 10 is not so limited. Many dental instruments in a dental office include connections to water sources or air sources, and so are not "cordless" as that term may be understood. However, foot controller 10 can be used with such dental instruments as well. Foot controller 10 as described above can be used as set forth above without modification. The dental instruments connected for use with water sources and/or air sources may be fitted with means for controlling the flow of air or water to the dental instrument. These means for controlling may include solenoid-controlled valves. The dental instruments may also be fitted with transceivers and microprocessors that can communicate with and receive signals from foot controller 10. The microprocessors can process signals received from foot controller 10 and provide instructions via the solenoid to control the flow of water or air based on operation of foot controller 10 by the dental professional. The flow of water and air simply be on or off, such as on when one of air, water or power is supplied to the dental instrument, or may be provided proportionally based on the flow of one of air, water or the power level of operation of the dental instrument.

Cordless foot controller of the present invention permits a dental station to utilize a single foot controller 10 to control a plurality of dental instruments, The number of dental instruments that foot controller 10 can control will depend on its memory capabilities, but its memory capabilities can be upgraded if desired. While the dental instruments may be cordless, foot controller 10 can be used to control air driven dental instruments as well as water flow to both air-driven dental instruments or electrically powered dental instruments. Foot controller 10 is programmable and may be programmed to learn the dental instruments with which it is to interact. Foot controller 10 may automatically recognize the dental instrument that is in the hand of the dental professional and will only operate the dental instrument in the hand of the dental professional, or the dental instrument that was last in the hand of the dental professional. Foot controller 10 will automatically enter a "sleep" mode after a predetermined period of inactivity in order to conserve battery life. Furthermore, the time period before "sleep" mode is entered may be selectable. While foot controller 10 is battery operated, it preferably utilizes a rechargable battery and includes an interface for recharging. The foot controller battery has sufficient power to allow operation a significantly longer period of time than the batteries used for dental instruments, about 30 days for a foot controller battery as compared to a full day for a dental instrument battery. However, future improvements in battery technology will increase the life expectancy of batteries used in both components. Foot controller 10 may be transported, and preferably includes sensors that sense when it is being transported. These sensors place foot controller 10 in a sleep mode when sensors determine that it is being transported to conserve battery power.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A wireless foot controller for communication with at least one wireless dental instrument, comprising:
    a housing;
    a power source positioned within the housing;
    a circuit board positioned within the housing and connected to receive power from the power source;
    an analog to digital signal converter;
    a microchip/controller associated with the circuit board;
    software to control the circuit board and the microchip/controller;
    an antenna for transmitting and receiving signals to and from the at least one wireless dental instrument;
    a communications protocol associated with the circuit board and the microchip/controller for communications between the foot controller and the at least one wireless dental instrument, wherein the foot controller is in communications with and controlling a single wireless dental instrument at a time;
    a memory for storing identification information received from the at least one dental instrument;
    wherein the foot controller is activated by application of foot pressure to depress the controller a distance proportional to the foot pressure;
    wherein the foot controller operates in a mode selected from the group consisting of a switch mode and a continuously variable mode
    wherein in the switch mode, the foot controller transmitting a signal resulting from switch activation in the switch mode and in the continuously variable mode, the foot controller transmitting a signal proportional to the distance that the foot controller is depressed; and
    wherein the foot controller software determines the selected mode based on an identification signal from the dental instrument and on the information stored in memory.

2. The wireless foot controller of claim 1 further includes a timing circuit that reduces power consumption from the power source to the foot controller when the foot controller is inactive for a predetermined length of time.

3. The wireless foot controller of claim 2 wherein the timing circuit is driven by the software.

4. The wireless foot controller of claim 2 further including a motion detection device that restores power consumption from the power source to the foot controller upon movement of the foot controller.

5. The wireless foot controller of claim 1 wherein the power source is a rechargeable battery.

6. The wireless foot controller of claim 5 further including a charge connector within the housing in electrical communication with the rechargeable battery for recharging the battery.

7. The wireless foot controller of claim 1 wherein the controller includes a bottom plate spaced from the cover wherein the bottom plate further comprises an anti-skid rubber bottom.

8. The wireless foot controller of claim 7 further including an upper housing within the cover and spaced from the bottom plate, the upper housing a plunger housing assembly in contact with the cover.

9. The wireless foot controller of claim 8 wherein the plunger housing assembly further includes a primary spring having a first spring constant and a secondary spring having a second spring constant nesting with respect to the primary spring, the plunger housing in contact with the cover so that pressure applied to the cover is resisted by at least one of the primary spring and the secondary spring, compression of the springs providing tactile feedback to a user.

10. The wireless foot controller of claim 1 wherein operation in the continuously variable mode includes a potentiometer in communication with the microchip/controller, wherein the microchip controller receives the signal from the potentiometer, and provides the signal to the antenna for transmission, the signal provided to the antenna proportional to the distance of depression of the foot pedal.

11. The wireless foot controller of claim 10 wherein the signal provided by the potentiometer is an analog signal, the analog signal being converted to a digital signal prior to transmission by the antenna.

12. The wireless foot controller of claim 9 further including a potentiometer for operation in the continuously variable mode, the potentiometer being responsive to the plunger housing, so that movement of the plunger housing assembly results in generation of the signal by the potentiometer, the signal being proportional to the distance that the plunger housing is moved with respect to the cover, which in turn is proportion to the distance that the foot controller is depressed.

13. The wireless foot controller of claim 9 wherein operation in the switch mode includes at least one switch in communication with the microchip/controller, wherein the microchip controller receives the signal from the switch, and provides the signal to the antenna for transmission, the switch providing the signal to the antenna upon depression of the foot pedal.

14. The wireless foot controller of claim 13 wherein the at least one switch includes a switch having multiple positions, wherein different positions of the switch are activated upon distance the foot controller is depressed, each position activated resulting in a generation of a different signal.

15. The wireless foot controller of claim 13 wherein the microchip/controller analyzes the signal received from the switch and provides a preselected signal to the antenna for transmission corresponding to the signal received from the switch.

16. The wireless foot controller of claim 13 wherein the signal transmitted by the antenna is a digital signal.

17. The wireless foot controller of claim 13 wherein the at least one switch includes a plurality of switches having locations, activation of the switch dependent upon the distance the foot controller is depressed, each switch generating a signal when activated.

18. The wireless foot controller of claim 17 wherein the microchip/controller analyzes the signal received from each activated switch, the microchip/controller providing a preselected signal to the antenna for transmission corresponding to the signal received.

19. The wireless foot controller of claim 9 including at least one switch for operation in the switch mode, the at least one switch being responsive to the plunger housing in contact with the cover and resisted by the primary spring to generate a first signal, and to the plunger housing assembly in contact with the cover and resisted by the secondary spring to generate a second signal.

* * * * *